United States Patent [19]

Knabe et al.

[11] 4,174,397
[45] Nov. 13, 1979

[54] THIAZOLIDINE DERIVATIVES

[75] Inventors: Bernd Knabe, Kelkheim; Hans-Jochen Lang, Hofheim am Taunas; Ernold Granzer, Kelkheim, all of Fed. Rep. of Germany

[73] Assignee: Hoechst Aktiengesellschaft, Frankfort am Main, Fed. Rep. of Germany

[21] Appl. No.: 830,774

[22] Filed: Sep. 6, 1977

[30] Foreign Application Priority Data

Sep. 8, 1976 [DE] Fed. Rep. of Germany ....... 2640358

[51] Int. Cl.$^2$ ............................................. C07D 277/60
[52] U.S. Cl. ..................................... 424/270; 548/150; 260/245.5; 548/149; 544/247
[58] Field of Search ................... 260/306.7 T; 424/270

[56] References Cited

U.S. PATENT DOCUMENTS

| | | | |
|---|---|---|---|
| 3,507,868 | 4/1970 | Manning | 260/251 |
| 4,061,647 | 12/1977 | Lang et al. | 260/306.7 T |
| 4,061,761 | 12/1977 | Lang et al. | 260/306.7 T |

OTHER PUBLICATIONS

Chemical Abstracts, vol. 76, (1972), 99605(e).

Primary Examiner—Nicholas S. Rizzo
Attorney, Agent, or Firm—Curtis, Morris & Safford

[57] ABSTRACT

Thiazolidine derivatives of the formula I

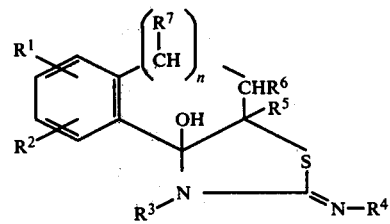

in which the substituents $R^1$ to $R^7$ have the meanings as indicated in the following and which have in the free form or in the form of their non toxic acid addition salts valuable pharmaceutical properties, processes for preparing them, pharmaceutical preparations on the basis of these compounds and their use as medicines.

11 Claims, No Drawings

THIAZOLIDINE DERIVATIVES

The present invention relates to thiazolidine derivatives of the general formula I

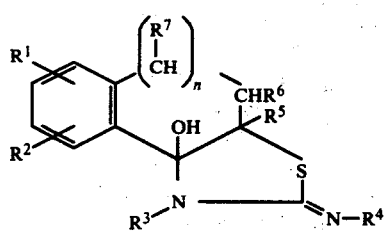

in which $R^1$ denotes hydrogen, a methyl group, halogen, trifluoromethyl or an alkoxy group with 1-3 C atoms, $R^2$ denotes hydrogen, a methyl group, halogen or a nitro group, $R^3$ and $R^4$ are the same or different and denote alkyl or alkenyl with 1-4 C atoms, phenylalkyl with 1-2 C atoms in the alkyl part or cycloalkyl with 3-6 C atoms, it also being possible for $R^3$ and $R^4$ to conjointly represent an optionally branched alkylene group with a total of 2-5 C atoms, $R^5$, $R^6$ and $R^7$ denote hydrogen or an alkyl radical with 1-3 C atoms and n can be 0-2, and acid addition salts thereof with pharmaceutically acceptable acids.

The invention furthermore relates to a process for the manufacture of the compounds of the general formula I, characterized in that (a) compounds of the general formula II

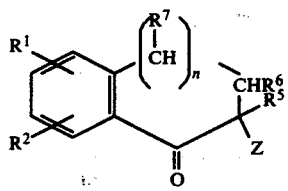

wherein $R^1$, $R^2$, $R^5$ to $R^7$ and n have the meaning indicated and Z represents the radical of an activated ester of an inorganic or organic acid, are reacted with thioureas of the general formula III, which can exist in the two tautomeric forms III a and III b

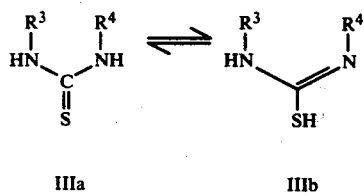

wherein $R^3$ and $R^4$ have the meaning indicated, or (b) compounds of the general formula IV

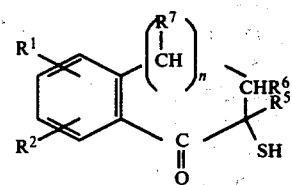

are reacted with compounds of the formula V

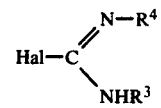

or with corresponding carbodiimides of the general formula VI $R^1$ to $R^7$ and n having the meaning indicated and Hal representing chlorine or bromine, or (c) compounds of the general formula VII

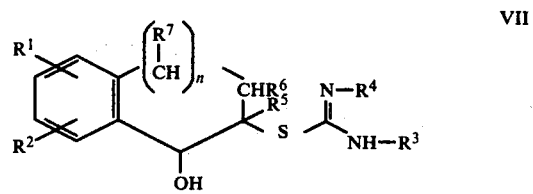

wherein $R^1$ to $R^7$ have the meaning indicated, are treated with an oxidizing agent, and, optionally the compounds of the general formula I, obtained according to (a) to (c), are converted, with organic or inorganic acids, into their acid addition salts or resulting salts of the compounds of the general formula I are converted, with bases, into the free basic compounds of the formula I.

Inorganic acids which can be used are, for example: hydrogen halide acids, such as hydrochloric acid and hydrobromic acid, as well as sulfuric acid, phosphoric acid and amidosulfonic acid.

Examples of organic acids which may be mentioned are: formic acid, acetic acid, benzoic acid, succinic acid, fumaric acid, maleic acid, lactic acid, tartaric acid, citric acid, salicylic acid, hydroxyethanesulfonic acid, ethylenediamine-tetraacetic acid, methanesulfonic acid, p-toluenesulfonic acid and the like.

The compounds of the formula I can also be present in their tautomeric forms:

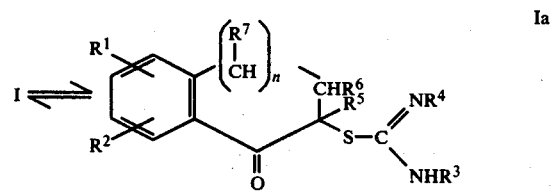

Moreover, the compounds, according to the invention, of the formula I can be present in their possible geometric isomeric structures.

The alkyl and alkenyl radicals in the substituents $R^1$ and $R^3$ to $R^7$ can be either straight-chain or branched.

In the case where $R^3$ and $R^4$ are different, the cyclic compounds of the formula I are in equilibrium, via the open-chain tautomeric form I a, with the compounds of the formula I b, which are position isomers, and acid addition salts thereof

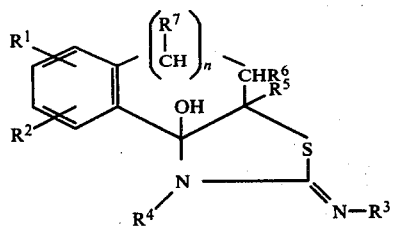

Which of the two cyclic isomers I or I b, or acid addition salts thereof, is preferentially present depends especially on the differing amount of space taken up by the substituents $R^3$ and $R^4$ in a manner such that the sterically smaller substituent is preferably in position 3 of the thiazolidine ring system. In the case of the compounds according to the invention, only one of the possible isomeric or tautomeric forms of a particular substance is indicated in the following text.

The procedure described under (a) is advantageously carried out by reacting the compounds II with the thioureas III in the molar ratio 1:1 to 1:1.5. The reaction is advantageously carried out in an inert solvent, such as, for example, in polar organic solvents, such as dimethylformamide, dimethylacetamide, dioxane, tetrahydrofuran, acetonitrile, nitromethane, diethylene glycol dimethyl ether and the like. However, acetic acid lower alkyl esters, such as acetic acid methyl ester and acetic acid ethyl ester, lower alcohols with 1–4 carbon atoms, especially methanol, ethanol and isopropanol, and lower dialkyl ketones, such as, for example, acetone and methyl ethyl ketone, have proved particularly advantageous reaction media. Mixtures of the solvents listed can also be used, and also mixtures of the solvents listed with solvents which in themselves are less suitable can be used, such as, for example, mixtures of methanol/benzene, ethanol/toluene, methanol/diethyl ether, ethanol/carbon tetrachloride and acetone/chloroform, in which the polar solvent should appropriately be present in excess. In this procedure, the reactants can be present suspended or dissolved in the particular solvent. In principle, the reactants can also be reacted without solvents, especially when the particular thiourea has as low a melting point as possible. The reaction proceeds moderately exothermically and can be carried out between 0° and 100°, preferably between 10° and 50°. A temperature range between 20° and 40° C. has proved particularly favorable.

The reaction time depends substantially on the reaction temperature and is between 2 minutes in higher temperature ranges and 60 hours at lower temperatures. In the favorable temperature range, the reaction time is generally between 5 minutes and 40 hours.

In the course of the reaction the compounds I, in the form of their acid addition salts, frequently separate out as sparingly soluble compounds; a suitable precipitating agent is appropriately also added subsequently. Such precipitating agents which can be used are, for example, hydrocarbons, such as benzene, toluene, cyclohexane, petroleum ether, ligroin and carbon tetrachloride; acetic acid lower alkyl esters with 1–4 carbon atoms in the alkyl part, such as acetic acid ethyl ester and acetic acid n-butyl ester, dialkyl ethers with 4–8 carbon atoms, such as, for example, diethyl ether, diisopropyl ether and di-n-butyl ether, in particular, have proved particularly suitable. If the mixture remains in the form of a solution after the reaction has ended, the salts of the compounds I are appropriately precipitated, if appropriate after concentrating the reaction solution, with one of the precipitating agents mentioned or the solution is advantageously filtered into one of the precipitating agents, whilst stirring. Since the reaction of the compounds II with the thioureas III proceeds virtually quantitatively, the resulting crude products are usually already analytically pure.

The compounds I can be recrystallized from an inert, suitable solvent, such as, for example, acetone, methyl ethyl ketone, acetonitrile or nitromethane. However, reprecipitation from a solvent, such as, for example, dimethylformamide, dimethylacetamide, nitromethane, acetonitrile or, preferably, methanol or ethanol, is particularly advantageous.

Most of the starting materials of the formula III are described in the literature. Those which were hitherto unknown are prepared in the customary manner by reacting amines with isothiocyanates, carbon disulfide or thiophosgene (compare Houben-Weyl, "Methoden der organischen Chemie" ("Methods of Organic Chemistry"), Volume 9, page 884, 4th edition, 1955). The melting points (uncorrected) of the new thioureas of the formula III are listed in the following table:

| | Thioureas III | |
|---|---|---|
| $R^3$ | $R^4$ | Melting point |
| $CH_3$ | ◁ | 108° C. |
| ▷ | ◁ | 144° C. |
| $CH_2=CH-CH_2-$ | ◁ | 106° C. |

Possible radicals Z of an activated ester in the compounds of the formula II are Cl, Br, I, $-O-CO-C_6H_4-NO_2$, $CH_3-SO_2-O-$, $C_2H_5-SO_2-O-$, $C_6H_5-SO_2-O-$ and $CH_3C_6H_4-SO_2-O-$. They can be obtained by several methods:

(1) Diazoketones of the general formula VIII

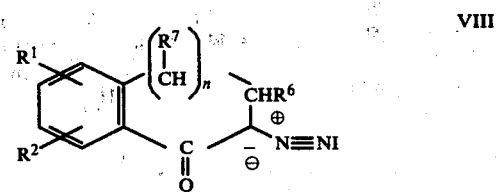

VIII can be converted into the compounds of the general formula II using hydrogen halide acids (Z=Cl, Br or I, $R^5$=H). This process and some compounds of the formula II are known from the literature (for example: J. Amer. Chem. Soc. 80, 2257 (1958) and J. Indian Chem. Soc. 42, 115 (1965)); the further compounds of the formula II can be correspondingly manufactured and reacted. Furthermore, the diazoketones of the general formula VIII can be converted via the hydroxy compounds of the general formula IX

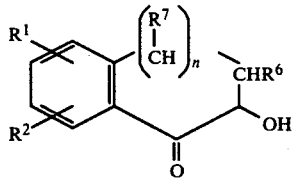

IX into the corresponding compounds of the formula II ($R^5=H$) by processes which are known from the literature.

(2) Since the processes mentioned under (1) only lead to compounds of the formula II in which $R^5$ remains limited to hydrogen, compounds of the formula II are advantageously manufactured by reacting compounds of the general formula X

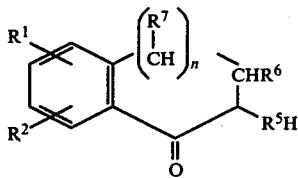

X with a suitable halogenating agent, such as, for example, with elementary chlorine or bromine, sulfuryl chloride, monochlorourea, copper-II bromide, bromodioxane, or N-bromosuccinimide, under conditions which are known from the literature. The conveniently accessible compounds X are either known or can be manufactured by processes from the literature.

Halogenating agents which can be used are, for example, elementary chlorine, sulfuryl chloride, monochlorourea, bromodioxane and N-bromosuccinimide, but in particular elementary bromine or copper-II bromide. In the halogenation with bromine, bromine, if appropriate diluted in inert solvents, is advantageously added dropwise to a solution or suspension of the equimolar amount of X in an inert solvent. Inert solvents which can be used are, for example, halogenohydrocarbons, such as chloroform or methylene chloride, but preferably glacial acetic acid or acetic acid lower alkyl esters, or mixtures of the solvents mentioned. The temperature is between 0° and 50° C., preferably between 10° and 35° C. Since ketone halogenations are catalyzed by acids, the reaction mixture is either seeded with catalytic amounts of an acid, for example with hydrobromic acid, or is initially warmed after the dropwise addition of a little bromine, until the halogen is decolorized, and then brominated further.

The bromination of the compounds X with copper-II bromide is carried out analogously to the method described in J. Org. Chem. 29, 3459 (1964).

A suitable chlorinating agent is, in particular, sulfuryl chloride, which is reacted, in the customary manner, with a solution or suspension of the compounds X in a solvent, such as, for example, chloroform or carbon tetrachloride, in a temperature range between 20° and 80° C. Ice-water is then added and the reaction mixture is worked up in the customary manner. When chlorine is used as the halogenating agent, HCl gas is initially passed, as the catalyst, into the solution of X in a polar solvent, for example glacial acetic acid or dimethylformamide, and then an equivalent amount of chlorine is passed in in a temperature range between 0° and 25° C. The reaction time is 2-24 hours. Ice-water is then added and the reaction mixture is worked up in the customary manner.

(3) Finally, the compounds of the formula II can also be obtained by reacting α-hydroxyketones of the general formula XI

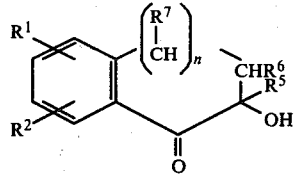

XI which are known, for example from Chem. Ber. 83, 390, or can be manufactured by conventional processes, with activated derivatives of organic and inorganic acids, such as methanesulfonic acid chloride, ethanesulfonic acid chloride, benzenesulfonic acid chloride, p-toluenesulfonic acid chloride, thionyl bromide, phosphorus trichloride, phosphorus tribromide, phosphorus oxychloride or p-nitrobenzoyl chloride, in a manner which is in itself known.

The solution or suspension of the compounds of the formula II, thus obtained by the respective method, is appropriately evaporated under reduced pressure and the compounds II are purified by crystallization in inert solvents, such as, for example, benzene, toluene, carbon tetrachloride, cyclohexane, petroleum ether and the like. However, the compounds II thus obtained are more advantageously reacted, without further purification operations, with the equimolar amount of thiourea III in a suitable inert solvent in the manner described above. If the halogenoketone II is reacted with the thioureas III without prior isolation, the amount of thiourea III to be used is calculated with respect to the particular ketone IX, X or XI.

The reaction, described in procedure (b), of the compounds of the formula IV with the known compounds of the formula V is carried out in a solvent. Suitable solvents are lower alcohols with 1-4 carbon atoms and lower alkyl esters of acetic acid with 1-4 carbon atoms in the alkyl part, such as, for example, acetic acid methyl ester and acetic acid ethyl ester.

The reactions are generally carried out in a temperature range between 0° and 60° C., preferably between 15° and 35° C., the reaction time being between 5 and 60 hours.

The reaction, described in procedure (b), of the mercaptoketones of the formula IV with the carbodiimides of the formula VI is carried out in an anhydrous, polar, inert solvent, for example in dioxane, tetrahydrofuran, acetic acid methyl ester or acetic acid ethyl ester, in the molar ratio 1:1 in a temperature range from 0° to 40° C., preferably between 10° and 30° C. The reaction time is between 1 and 20 hours. Reaction products which precipitate in the crystalline form are filtered off and optionally recrystallized. Otherwise the reaction solution is concentrated and the residues are recrystallized.

The free bases obtained as end products can be optionally converted into the corresponding salts by treatment with inorganic and organic acids.

The compounds of the formula IV used according to procedure (b) are manufactured by processes which are known from the literature. Thus the compounds of the formula II can be converted, with thiocarboxylic acids of the formula XII

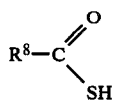   XII preferably with thioacetic acid ($R^8=CH_3$) in the presence of one equivalent of a base, for example of KOH, in an aqueous or alcoholic medium, into the thioesters of the general formula XIII, which are hydrolyzed in a weakly alkaline medium to the compounds of the formula IV.

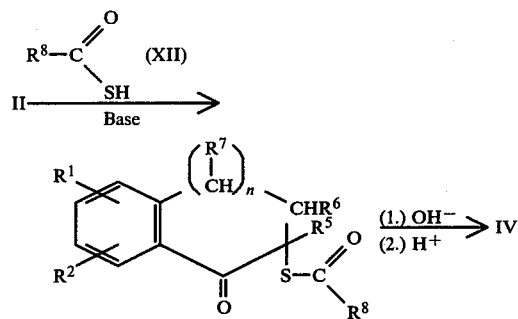   XIII

Another possibility consists in reacting the compounds II with alkali metal hydrogen sulfides in an inert solvent, such as, for example, sodium hydrogen sulfide or potassium hydrogen sulfide in dimethylformamide, at temperatures between 0° and 40° C. The processes which lead to the compounds IV are known from the literature.

Active manganese-IV oxide is preferably used as the oxidizing agent according to procedure (c). Halogenated hydrocarbons, such as, for example, methylene chloride, chloroform or tetrachloroethane, are preferably used as the solvent, the reaction being carried out at temperatures between 0° and 40° C., preferably between 20° and 30° C., over a period of 10 to 60 hours.

The starting materials of the formula VII are obtained, for example, by converting halogenoketones of the formula II, wherein Z preferably represents chlorine or bromine, into the compounds of the formula XIV

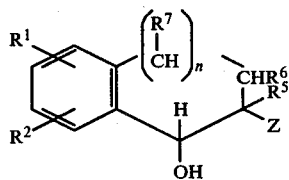   XIV wherein Z represents halogen, for example according to Arzneimittel-Forsch. 22, 2095 (1972) with a suitable reducing agent, preferably with sodium borohydride in methanol, at temperatures between 0° and 25° C. The compounds XIV react with thioureas of the formula III to give the isothiouronium salts of the formula VII.

The reaction conditions correspond to those for procedure (a).

The compounds I can be recrystallized from an inert, suitable solvent, such as, for example, acetone, methyl ethyl ketone, acetonitrile or nitromethane. However, reprecipitation from a solvent, such as, for example, dimethylformamide, dimethylacetamide, nitromethane, acetonitrile or, preferably, methanol or ethanol, is particularly advantageous.

The compounds of the formula I can be optionally converted, with an acid of the formula H—X, into their salts. For this, it is possible to introduce the compounds I into the pure acids at temperatures between 0° and 40° C. if these acids are liquid or have a melting point which is not substantially higher than 40° C. However, the reaction is advantageously carried out in a solvent, such as, for example, in water or an organic solvent, such as, for example, in dioxane, tetrahydrofuran, ether, an acetic acid lower alkyl ester with 1–4 carbon atoms in the alkyl part, acetonitrile, nitromethane, acetone or methyl ethyl ketone; however, lower alcohols with 1–4 carbon atoms are particularly suitable. In this procedure, 1–1.5 moles of the acid H—X are used per mole of the compounds I, but it is also possible to use larger amounts of acid. The reaction is appropriately carried out at temperatures between 0° and 40° C., preferably between 10° and 25° C. The reaction is moderately exothermic.

When the reaction is carried out in an aqueous solution, after adding acids H—X the compounds I generally dissolve immediately and the corresponding acid addition compounds only seldom separate out. When a solution is obtained, the salts according to the invention are appropriately isolated by carefully evaporating off the water, preferably by freeze-drying. When the reaction is carried out in organic solvents, the acid addition salts frequently separate out as sparingly soluble compounds, after adding the particular acid H—X. Otherwise the acid addition compounds are separated out, if appropriate after prior concentration, with one of the precipitating agents mentioned.

Even when they have a very high degree of purity, the acid addition products are occasionally obtained in the form of viscous oils or amorphous vitreous products. These amorphous products can be brought to crystallization with treatment with an organic solvent at 40° to 80° C. Solvents which are suitable for this are, in particular, acetic acid lower alkyl esters with 1–4 carbon atoms in the alkyl part, lower dialkyl ketones, such as acetone or methyl ethyl ketone, lower dialkyl ethers and acetonitrile, nitromethane and if appropriate also lower alcohols.

The acid addition products can be deprotonated by treatment with bases to give the compounds of the general formula I. Bases which can be used are, for example, solutions of inorganic hydroxides, such as lithium hydroxide, sodium hydroxide, potassium hydroxide, calcium hydroxide or barium hydroxide, carbonates or bicarbonates, such as sodium carbonate, potassium carbonate, sodium bicarbonate or potassium bicarbonate, ammonia and amines, such as triethylamine, dicyclohexylamine, piperidine or methyldicyclohexylamine.

When the reaction is carried out in an aqueous medium, the free basic compounds I frequently separate out as sparingly soluble compounds and can be separated off by filtration or by extraction with an organic solvent, preferably with acetic acid ethyl ester, and isolated. Suitable organic reaction media are, in particular, lower alcohols with 1–4 carbon atoms, preferably methanol and ethanol, but ethyl acetate, diethyl ether, tetrahydrofuran, dioxane, diethylene glycol dimethyl ether, dimethylformamide and many others can also be used. The reaction is carried out between −35° and +60° C., preferably between 0° and 25° C. If a water-miscible organic solvent is used, the free bases of the formula I are precipitated, if appropriate after prior concentration of the reaction mixture, by adding water. If a solvent which is not water-miscible is used, after the reaction the reaction mixture is washed with water and the organic solent is evaporated off.

In addition to the derivatives described in the examples of carrying out the invention, the compounds of the general formula I, or acid addition products thereof, listed in the tables which follow, can, for example, also be obtained according to the invention:

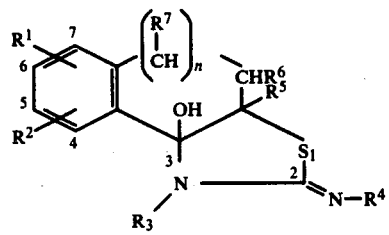

I

| | n | $R^1$ | $R^2$ | $R^3$ | $R^4$ | $R^5$ | $R^6$ | $R^7$ |
|---|---|---|---|---|---|---|---|---|
| 1 | 0 | 6-Cl | H | —CH₂—CH₂—C(CH₃)₂— | | H | H | — |
| 2 | 0 | 6-Cl | H | | —(CH₂)₄— | H | H | — |
| 3 | 0 | 6-Cl | H | CH₃CH₂CH₂— | CH₃CH₂—CH₂— | H | H | — |
| 4 | 0 | 6-Cl | H | (CH₃)₂CH— | (CH₃)₂CH— | H | H | — |
| 5 | 0 | 6-Cl | H | n-C₄H₉— | n-C₄H₉ | H | H | — |
| 6 | 0 | 6-Cl | H | i-C₄H₉ | i-C₄H₉ | H | H | — |
| 7 | 0 | 6-Cl | H | C(CH₃)₃— | C(CH₃)₃— | H | H | — |
| 8 | 0 | 6-Cl | H | CH₃ | C₂H₅ | H | H | — |
| 9 | 0 | 6-Cl | H | CH₃ | ▷— | H | H | — |
| 10 | 0 | 6-Cl | H | CH₃ | (CH₃)₂CH— | H | H | — |
| 11 | 0 | 6-Cl | H | CH₂=CH—CH₂ | ▷— | H | H | — |
| 12 | 0 | 6-Cl | H | C₂H₅ | (CH₃)₃C— | H | H | — |
| 13 | 0 | 6-Cl | H | C₂H₅ | (CH₃)₂CH— | H | H | — |
| 14 | 0 | 6-Cl | H | CH₃ | ⬡—H | H | H | — |
| 15 | 0 | 6-Cl | H | CH₃ | ▢— | H | H | — |
| 16 | 0 | 6-Cl | H | C₂H₅ | ⬠— | H | H | — |
| 17 | 0 | 6-Cl | H | (CH₃)₂CH | ▷— | H | H | — |
| 18 | 0 | 6-Cl | H | (CH₃)₂CH | n-C₄H₉— | H | H | — |
| 19 | 0 | 6-Cl | H | CH₃—CH₂—CH₂— | ▢— | H | H | — |
| 20 | 0 | 6-Cl | H | n-C₄H₉ | ⬡—H | H | H | — |
| 21 | 0 | 6-Cl | H | C(CH₃)₃— | ⬠— | H | H | — |
| 22 | 0 | 6-Cl | H | ▷— | ⬠— | H | H | — |
| 23 | 0 | 6-Cl | H | ▷— | ▢— | H | H | — |

-continued

I

| | n | R¹ | R² | R³ | R⁴ | R⁵ | R⁶ | R⁷ |
|---|---|---|---|---|---|---|---|---|
| 24 | O | 6-Cl | H | cyclopentyl | cyclopentyl | H | H | — |
| 25 | O | 6-Cl | H | cyclopentyl | cyclohexyl | H | H | — |
| 26 | O | 6-Cl | H | CH₃ | CH₃ | CH₃ | H | — |
| 27 | O | 6-Cl | H | C₂H₅ | C₂H₅ | CH₃ | H | — |
| 28 | O | 6-Cl | H | | —CH₂—CH₂— | CH₃ | H | — |
| 29 | 0 | 6-Cl | H | CH₃ | phenyl-CH₂— | CH₃ | H | — |
| 30 | O | 6-Cl | H | CH₃ | CH₃ | C₂H₅ | H | — |
| 31 | O | 6-Cl | H | | —CH₂—CH₂— | C₂H₅ | H | — |
| 32 | O | 6-Cl | H | C₂H₅ | C₂H₅ | H | C₂H₅ | — |
| 33 | O | 6-Cl | H | CH₂=CH—CH₂— | CH₂=CH—CH₂— | H | C₂H₅ | — |
| 34 | O | 6-Cl | H | CH₃ | CH₃ | H | CH₃ | — |
| 35 | O | 6-Cl | H | C₂H₅ | C₂H₅ | H | CH₃ | — |
| 36 | O | 6-Cl | H | | —CH₂—CH₂— | H | CH₃ | — |
| 37 | O | 6-Cl | H | | —CH₂—CH₂— | H | C₂H₅ | — |
| 38 | O | 6-Cl | H | CH₃ | CH₃ | CH₃ | CH₃ | — |
| 39 | O | 6-Cl | H | CH₃ | CH₃ | C₂H₅ | CH₃ | — |
| 40 | O | 6-Cl | H | | —CH₂—CH₂— | CH₃ | CH₃ | — |
| 41 | O | 4-Cl | H | CH₃ | CH₃ | H | H | — |
| 42 | O | 4-Cl | H | | —CH₂—CH₂— | H | H | — |
| 43 | O | 6-CH₃ | H | CH₃ | CH₃ | H | H | — |
| 44 | O | 6-CH₃ | H | C₂H₅ | C₂H₅ | H | H | — |
| 45 | O | 6-CH₃ | H | | —CH₂—CH₂— | H | H | — |
| 46 | O | 6-CH₃ | H | CH₂=CH—CH₂— | CH₂=CH—CH—CH₂— | H | H | — |
| 47 | O | 6-F | H | CH₃ | CH₃ | H | H | — |
| 48 | O | 6-F | H | | —CH₂—CH₂— | H | H | — |
| 49 | O | 6-Br | H | CH₃ | CH₃ | H | H | — |
| 50 | O | 6-Br | H | C₂H₅ | C₂H₅ | H | H | — |
| 51 | O | 6-Br | H | CH₃ | phenyl-CH₂— | H | H | — |
| 52 | O | 6-Br | H | | —CH₂—CH₂— | H | H | — |
| 53 | O | 6-CF₃ | H | CH₃ | CH₃ | H | H | — |
| 54 | O | 6-CF₃ | H | C₂H₅ | C₂H₅ | H | H | — |
| 55 | O | 6-CF₃ | H | | —CH₂—CH₂— | H | H | — |
| 56 | O | 5-CF₃ | H | CH₃ | CH₃ | H | H | — |
| 57 | O | 5-CF₃ | H | | —CH₂—CH₂— | H | H | — |
| 58 | O | 6-OC₂H₅ | H | CH₃ | CH₃ | H | H | — |
| 59 | 0 | 6-OC₂H₅ | H | cyclopropyl | cyclopropyl | H | H | — |
| 60 | O | 6-OC₂H₅ | H | | —CH₂—CH₂— | H | H | — |
| 61 | O | 6-OC₂H₅ | H | C₂H₅ | C₂H₅ | H | H | — |
| 62 | O | 6-OCH₃ | H | CH₃ | CH₃ | CH₃ | H | — |
| 63 | O | 6-OCH₃ | H | | —CH₂—CH₂— | CH₃ | H | — |
| 64 | O | 6-OCH₃ | H | CH₃ | CH₃ | H | CH₃ | — |
| 65 | O | 6-OCH₃ | H | | —CH₂—CH₂— | H | CH₃ | — |
| 66 | O | 5-OCH₃ | H | CH₃ | CH₃ | H | H | — |
| 67 | O | 5-OCH₃ | H | | —CH₂—CH₂— | H | H | — |
| 68 | O | 6-Cl | 5-Cl | CH₃ | CH₃ | H | H | — |
| 69 | O | 6-Cl | 5-Cl | C₂H₅ | C₂H₅ | H | H | — |
| 70 | O | 6-Cl | 5-Cl | | —CH₂—CH₂— | H | H | — |

-continued $$\text{I}$$

Structure: Benzene ring with R¹ at position 7, R² at position 4 (via positions 5,6), with (CH(R⁷))ₙ and CHR⁶R⁵ substituents; central carbon bearing OH (position 3) connected to N(R₃) and to S₁–C₂=N–R⁴ ring.

| n | R¹ | R² | R³ | R⁴ | R⁵ | R⁶ | R⁷ |
|---|---|---|---|---|---|---|---|
| 71 | 0 | 6-Cl | 5-Cl | CH₃ | —C₆H₄—CH₂— (benzyl) | H | H | — |
| 72 | 0 | H | 5-NO₂ | CH₃ | benzyl-CH₂— | H | H | — |
| 73 | 0 | 6-Cl | 5-NO₂ | cyclopropyl | cyclopropyl | H | H | — |
| 74 | 0 | 6-Cl | 5-NO₂ | CH₃ | benzyl-CH₂— | H | H | — |
| 75 | 0 | 6-Cl | 5-NO₂ | CH₃ | CH₃ | H | CH₃ | — |
| 76 | 0 | 6-Cl | 5-NO₂ |  | —CH₂—CH₂— | CH₃ | H | — |
| 77 | 0 | 5-CH₃ | H | CH₃ | CH₃ | H | H | — |
| 78 | 0 | 6-CH₃ | 5-NO₂ | CH₃ | CH₃ | H | H | — |
| 79 | 0 | 6-CH₃ | 5-NO₂ |  | —CH₂—CH₂— | H | H | — |
| 80 | 0 | 6-OCH₃ | 5-NO₂ | CH₃ | CH₃ | H | H | — |
| 81 | 0 | 6-OCH₃ | 5-NO₂ |  | —CH₂—CH₂— | H | H | — |
| 82 | 0 | 6-OCH₃ | 5-Cl | CH₃ | benzyl-CH₂— | H | H | — |
| 83 | 1 | 6-Br | H | CH₃ | CH₃ | H | H | H |
| 84 | 1 | 5-Br | H | CH₃ | CH₃ | H | H | H |
| 85 | 1 | 6-CH₃ | H | CH₃ | CH₃ | H | H | H |
| 86 | 1 | 6-CH₃ | H |  | —(CH₂)₂— | H | H | H |
| 87 | 1 | 5-CH₃ | H | CH₃ | CH₃ | H | H | H |
| 88 | 1 | 5-CH₃ | H |  | —(CH₂)₂— | H | H | H |
| 89 | 1 | 5-CH₃ | 6-CH₃ | CH₃ | CH₃ | H | H | H |
| 90 | 1 | 5-CH₃ | 6-CH₃ |  | —(CH₂)₂— | H | H | H |
| 91 | 1 | 5-Cl | 5-Cl | CH₃ | CH₃ | H | H | H |
| 92 | 1 | 5-CH₃ | 6-CH₃ |  | —(CH₂)₃— | H | H | H |
| 93 | 1 | 5-Cl | 5-Cl |  | —(CH₂)₂— | H | H | CH₃ |

The process products are valuable medicaments and are distinguished by favorable effects on lipid metabolism; they are particularly suitable for use as anorectic agents, which, surprisingly, are superior to the known thiazolidine derivatives (for example from German Offenlegungsschrift No. 1,938,674 and U.S. Pat. No. 3,671,534).

The appetite-inhibiting action of the new compound is demonstrated in a pharmacological test, when administered perorally and/or intraperitoneally to rats which had fasted for 48 hours, by an inhibition in the feed intake. In the case of semi-chronic administration, an inhibition of the increase in body weight could be observed.

In the test for appetite-inhibiting action, the feed consumption of fasting rats placed in individual cages was measured hourly for 6 hours after administration of the compounds. Solutions or suspensions of the test substances were administered to, in each case, 6 rats, orally by means of a stomach tube or intraperitoneally, in different dosages (mg/kg of body weight). 30 minutes after intraperitoneal administration or 1 hour after peroral administration the animals were offered a precisely measured amount of pelletted feed and the amount of feed eaten was determined hourly for 6 hours by re-weighing the amount of feed placed in the cages. The average value for the group at each time of determining the feed consumption was obtained from the feed consumption of each individual animal. This average value of feed consumption was compared with that of a simultaneous control group which had only received the solvent or suspending agent. The differences compared with the control group are given in % in the tables which follow. (In the determination of the appetite-inhibiting action, the compounds were employed in the form of their salts, that is to say hydrochlorides or hydrobrimides; both salts are to be regarded as equivalent in the experiments).

Table 1

| Compound according to Example | Dosage (mg/kg) per-orally | % difference compared with the control group after | | | | | |
|---|---|---|---|---|---|---|---|
| | | 1 | 2 | 3 | 4 | 5 | 6 hours |
| 1 or 2 | 100 | −73 | −65 | −64 | −62 | −59 | −55 |
|  | 30 | −58 | −35 | −31 | −30 | −31 | −24 |
|  | 10 | −27 | −23 | −25 | −19 | −14 | −10 |
|  | 3 | −24 | −21 | −20 | −23 | −15 | − 4 |
|  | 1 | −16 | −23 | −31 | −22 | −11 | −18 |
| 9 | 100 | −58 | −37 | −36 | −22 | −30 | −33 |
|  | 10 | −49 | −43 | −27 | − 7 | −18 | −13 |
| 11 | 100 | −79 | −58 | −42 | −40 | −32 | −34 |
| 15 | 100 | −66 | −46 | −55 | −44 | −40 | −41 |
|  | 30 | −58 | −46 | −42 | −26 | −18 | −15 |
|  | 10 | ± 0 | −14 | −15 | − 4 | −14 | −13 |
|  | 30 | −64 | −48 | −37 | −29 | −21 | −10 |
| 10 or 28 | 10 | −64 | −37 | −26 | −25 | −21 | −13 |
|  | 3 | −28 | −28 | −30 | −28 | −20 | −10 |
|  | 1 | −32 | −26 | −35 | −32 | −26 | −26 |

Table 2

| Compound according to Example | Dosage (mg/kg) intra-peritone-ally | % difference compared with the control group after | | | | | |
|---|---|---|---|---|---|---|---|
| | | 1 | 2 | 3 | 4 | 5 | 6 hours |
|  | 10 | −64 | −46 | −45 | −39 | −32 | −40 |
| 1 or 2 | 3 | −43 | −26 | −15 | −19 | − 7 | −11 |
|  | 1 | −43 | −16 | −16 | − 7 | − 8 | −12 |
| 8 | 100 | −100 | −100 | −100 | −94 | −90 | −88 |
|  | 10 | −25 | −11 | −26 | −10 | −13 | −14 |
|  | 3 | −15 | −31 | −26 | −20 | −22 | −25 |
| 11 | 30 | −70 | −79 | −69 | −59 | −47 | −45 |
|  | 3 | +11 | −31 | −35 | −33 | −34 | −31 |
| 15 | 30 | −74 | −84 | −55 | −48 | −32 | −29 |
|  | 3 | −65 | −52 | −41 | −33 | −38 | −35 |
|  | 30 | −69 | −73 | −63 | −62 | −58 | −61 |
| 10 or 28 | 10 | −59 | −43 | −29 | −23 | −20 | −24 |
|  | 3 | −54 | −48 | −21 | −25 | −22 | −16 |
|  | 1 | −50 | −42 | −24 | −14 | − 7 | −10 |

In addition to the very good appetite-inhibiting action of the process products, a favorable action on lipid metabolism disorders is frequently observed.

The compounds can thus be employed as appetite-inhibitors for the treatment of obesity alone or accompanied by other lipid metabolishm disorders. The dose to be administered daily is 2 to 2,000 mg, preferably 2–200 mg, this amount appropriately being administered in smaller doses of 0.5–50 mg 2 to 4 times daily or in a delayed release form.

Therapeutical formulations of the new compounds which can be used are, above all, tablets, dragees, and capsules for oral administration ampoules for parenteral adiministration and suppositories. These formulations preferably contain the process products in the form of their acid addition products.

The examples given in the following text serve to illustrate the invention without, however, limiting it. The decomposition points indicated are uncorrected and generally depend on the rate of heating.

EXAMPLE 1

6-Chloro-3a-hydroxy-3-methyl-2-methylimino-indano[2,1-b]-thiazolidine hydrobromide (a) 2-Bromo-5-chloro-1-indanone A solution of 37.9 g (0.237 mole) of bromine in 120 ml of glacial acetic acid is slowly added dropwise, whilst stirring, to a solution of 40.0 g (0.237 mole) of 5-chloro-1-indanone in 590 ml of glacial acetic acid, to which 0.2 ml of 48% strength aqueous hydrobromic acid has been added. The mixture is stirred for a further 2 hours and the reaction solution is poured into 1 l of water, to which 2.5 g of NaHSO$_3$ have been added. The product, which initially precipitates in the viscous form, becomes crystalline after stirring for a relatively long time. The crude product is filtered off (melting point 69°–76° C.), washed with water and recrystallized from petroleum ether. The pure 2-bromo-5-chloro-1-indanone melts at 89°–90° C.

(b) 6-Chloro-3a-hydroxy-3-methyl-2-methylimino-indano[2,1-b]-thiazolidine hydrobromide A solution of 1.05 g (10 mmoles) of N,N'-dimethylthiourea in 20 ml of acetone is added to a solution of 2.47 g (10 mmoles) of 2-bromo-5-chloro-1-indanone (Example 1 (a)) in 30 ml of acetone at room temperature.

After some time, a colorless precipitate begins to separate out from the solution. The mixture is subsequently stirred for a total of 5 hours and the precipitate is filtered off. The colorless product of decomposition point 148°–150° is reprecipitated from methanol/ether, after which the pure compound of decomposition point 181°–183° C. is obtained.

EXAMPLE 2

6-Chloro-3a-hydroxy-3-methyl-2-methylimino-indano-[2,1-b]-thiazolidine hydrochloride A 2 N NaOH solution is added dropwise to a suspension of 0.5 g (1.43 mmoles) of 6-chloro-3a-hydroxy-3-methyl-2-methylimino-indano-[2,1-b]-thiazolidine hydrobromide (Example 1) in 10 ml of water until the pH value is 9.5. The mixture is subsequently stirred for 15 minutes and the precipitate is filtered off and dissolved in ether. The ether solution is dried and then concentrated to dryness. The residue is suspended in 10 ml of acetone and ethereal hydrochloric acid is then added, whereupon a clear solution forms from which, on triturating and after stirring for a relatively long time, the end product precipitates. The precipitate is filtered off and the end compound of decomposition point 265°–267° C. is obtained.

EXAMPLE 3

3-Ethyl-2-ethylimino-6-chloro-3a-hydroxy-indano-[2,1-b]-thiazolidine hydrobromide Analogously to Example 1 (b), 4.94 g (20 mmoles) of 2-bromo-5-chloro-1-indanone (Example 1 (a)) in 30 ml of acetone and 2.64 g (20 mmoles) of N,N'-diethylthiourea in 30 ml of acetone give the crystalline colorless end product of decomposition point 178°–181° C.

EXAMPLE 4

3-Benzyl-2-benzylimino-6-chloro-3a-hydroxy-indano[2,1-b]-thiazolidine hydrobromide In accordance with the procedure described in Example 1b), 4.94 g (20 mmoles) of 2-bromo-5-chloro-1-indanone (Example 1a) in 30 ml of acetone and 5.12 g (20 mmoles) of N,N'-dibenzylthiourea in 30 ml of acetone give the crystalline end product of decomposition point 184°–186° C.

EXAMPLE 5

3a-Hydroxy-3-methyl-2-methylimino-5-nitro-indano[2,1-b]-thiazolidine hydrobromide

(a) 2-Bromo-6-nitro-1-indanone

Analogously to Example 1 (a), reaction of 12.39 g (70.0 mmoles) of 6-nitro-1-indanone in 130 ml of glacial acetic acid, containing 0.5 ml of 48% strength aqueous hydrobromic acid, and 11.2 g (70 mmoles) of bromine in 70 ml of glacial acetic acid, in accordance with the instructions indicated above, gives 2-bromo-6-nitro-1-indanone of melting point 102°–105° C. which, as the pure product after reprecipitation from ethanol/water, has a melting point of 114°–116° C.

(b) 3a-Hydroxy-3-methyl-2-methylimino-5-nitro-indano[2,1-b]-thiazolidine hydrobromide Analogously to Example 1 (b), 3.84 g (15 mmoles) of 2-bromo-6-nitro-1-indanone in 50 ml of acetone and 1.57 g (15 mmoles) of N,N'-dimethylthiourea give the crystalline end product of decomposition point 192°–193°, which after reprecipitation from methanol/ether has a decomposition point of 200°–205° C.

EXAMPLE 6

5a-Hydroxy-3,4-dihydro-7-nitro-indano-[2,1-b]-imidazo-[1,2-d]-thiazolidine hydrobromide In accordance with the procedure indicated in Example 1 (b), 3.84 g (15 mmoles) of 2-bromo-6-nitro-1-indanone (Example 5) in 50 ml of acetone and 1.53 g (15 mmoles) of 2-imidazolidine-thione in 40 ml of acetone give the crystalline end compound which, after reprecipitation from methanol/ether, decomposes at 220°.

EXAMPLE 7

5-Chloro-3a-hydroxy-3-methyl-3-methylimino-indano-[2,1-b]-thiazolidine hydrobromide

(a) 2-Bromo-6-chloro-1-indanone

A solution of 9.59 g (60.0 mmoles) of bromine in 20 ml of acetic acid ethyl ester is added dropwise to a solution of 10.0 g (60.0 mmoles) of 6-chloro-1-indanone in 80 ml of acetic acid ethyl ester and 0.5 ml of 48% strength aqueous hydrobromic acid. After stirring for 3 hours, the reaction solution is concentrated to dryness, the residue is stirred with 50 ml of water and the precipitate is filtered off. The crude product of melting point 84°–87° is recrystallized from petroleum ether 60/70 and gives the pure product of melting point 92°–94° C.

(b) 5-Chloro-3a-hydroxy-3-methyl-3-methylimino-indano-[2,1-b]-thiazolidine hydrobromide The crude product obtained by reacting 4.92 g (20 mmoles) of 2-bromo-6-chloro-1-indanone in 50 ml of acetone with 2.10 g (20 mmoles) of N,N'-dimethylthiourea in 20 ml of acetone analogously to Example 1 (b) is reprecipitated from methanol/ether. The pure colorless substance decomposes at 120°–123° C.

EXAMPLE 8

3-Allyl-2-allylimino-6-chloro-3a-hydroxy-indano-[2,1-b]-thiazolidine hydrobromide Analogously to Example 1 (b), 2.47 g (10 mmoles) of 2-bromo-5-chloro-1-indanone (Example 1a) in 20 ml of acetone and 1.56 g (10 mmoles) of N,N'-diallylthiourea give the colorless crystalline end product with a decomposition point of 158° C.

EXAMPLE 9

9-Chloro-6a-hydroxy-4,5-dihydro-3H-indano-[1',2':4,5]-thiazolidino[3,2-a]-pyrimidine hydrobromide A suspension of 2.32 g (20 mmoles) of 3,4,5,6-tetrahydro-2-pyrimidine-thiol in 20 ml of acetone is added to a solution of 4.94 g (20 mmoles) of 2-bromo-5-chloro-1-indanone (Example 1 (a)) in 50 ml of acetone and the mixture is stirred for 5 hours. The precipitate is filtered off and the crude product (decomposition point 211°–219° C.) is reprecipitated from methanol/ether. The pure compound decomposes at 225°–226° C.

EXAMPLE 10

8-Chloro-5a-hydroxy-3,4-dihydro-indano-[2,1-b]-imidazo-1,2-d]-thiazolidine hydrobromide Analogously to Example 9, 4.94 g (20 mmoles) of 2-bromo-5-chloro-1-indanone (Example 1a) in 30 ml of acetone and 2.04 g (20 mmoles) of 2-imidazolidine-thione in 30 ml of acetone give the crude product of decomposition point 272°–274° C. which, after reprecipitation from methanol/ether, gives the pure compound, decomposition point 276°–278°.

EXAMPLE 11

8-Chloro-5a-hydroxy-3,4-dihydro-3,3-dimethyl-3H-indano-[2,1-b]-imidazo-[1,2-d]-thiazolidine hydrobromide 1.95 g (15 mmoles) of 5,5-dimethyl-2-imidazolidinethione are added to a solution of 3.69 g (15 mmoles) of 2-bromo-5-chloro-1-indanone (Example 1a), the solution is stirred for 3 hours, the suspension formed is left to stand overnight and the precipitate is filtered off and washed with acetone.

The colorless crystalline product decomposes at 170°–171° C.

EXAMPLE 12

6-Chloro-3-cyclohexyl-2-cyclohexylimino-3a-hydroxy-indano-[2,1-b]-thiazolidine hydrobromide

(a) 5-Chloro-2-mercapto-1-indanone

A solution of 1.37 g (18 mmoles) of thioacetic acid in 30 ml of ethanol is neutralized exactly, in a nitrogen atmosphere, by the dropwise addition of a 40% strength aqueous KOH solution, and 3.7 g (15 mmoles) of 2-bromo-5-chloro-1-indanone (Example 1 (a)) are added. The reaction mixture is stirred for 1 hour at room temperature and poured into 200 ml of water. The product which crystallizes after some time is filtered off and introduced, under nitrogen, into 35 ml of a 5% strength aqueous NaOH solution. After stirring for 1 hour at room temperature, the pH is adjusted to 1 with 2 N hydrochloric acid and the crystalline precipitate is filtered off. The resulting 5-chloro-2-mercapto-1-indanone decomposes at 173°–175° C.

(b) 6-Chloro-3-cyclohexyl-2-cyclohexylimino-3a-hydroxy-indano-[2,1-b]-thiazolidine hydrobromide 2.06 g (10 mmoles) of dicyclohexylcarbodiimide are added in portions to a solution of 1.98 g (10 mmoles) of 5-chloro-2-mercapto-1-indanone in 30 ml of absolute tetrahydrofuran, the reaction temperature being kept at 10°–15° C. The reaction mixture is stirred for 2 hours at room temperature, left to stand for 24 hours at 0° C. and then stirred for a further 5 hours at room temperature. The solution is concentrated to dryness, water is added to the viscous residue and the pH of the suspension is adjusted to 1 with 48% strength aqueous hydrobromic acid. The resulting solid mass crystallizes on stirring with a little methanol and gives the end product of decomposition point 198°–200° C.

EXAMPLE 13

7-Chloro-3a-hydroxy-3-methyl-2-methylimino-indano-[2,1-b]-thiazolidine hydrobromide In accordance with the procedure indicated in Example 1 (b), 4.92 g (20 mmoles) of 2-bromo-4-chloro-1-indanone in 50 ml of acetone and 2.10 g (20 mmoles) of N,N'-dimethylthiourea in 30 ml of acetone gives the colorless crystalline end compound of decomposition point 273°–274° C.

EXAMPLE 14

9-Chloro-5a-hydroxy-3,4-dihydro-indano-[2,1-b]-imidazo-[1,2-d]-thiazolidine hydrobromide Analogously to Example 9, 4.92 g (20 mmoles) of 2-bromo-4-chloro-1-indanone in 50 ml of acetone and 2.04 g (20 mmoles) of 2-imidazolidine-thione give the crystalline end product of decomposition point 276°–277° C.

EXAMPLE 15

3a-Hydroxy-3-methyl-2-methylimino-indano-[2,1-b]-thiazolidine hydrobromide

Analogously to Example 1 (b), 4.22 g (20 mmoles) of 2-bromo-1-indanone in 30 ml of acetone and 2.08 g (20 mmoles) of N,N'-dimethylthiourea in 20 ml of acetone give the crystalline end product, decomposition point 250°–252°, which, after reprecipitation from methanol/ether, decomposes at 265°–267° C.

EXAMPLE 16

5a-Hydroxy-3,4-dihydro-indano-[2,1-b]-imidazo-[1,2-d]-thiazolidine hydrobromide

Reacting 4.22 g (20 mmoles) of 2-bromo-1-indanone in 50 ml of acetone with 2.04 g (20 mmoles) of 2-imidazolidinethione analogously to Example 9, the reaction mixture being further left to stand for several hours after stirring for 6 hours, gives the reaction product, decomposition point 243°–247° C., which, after reprecipitation from methanol/ether, decomposes at 263°–264° C.

EXAMPLE 17

3a-Hydroxy-6-methoxy-3-methyl-2-methylimino-indano-[2,1-b]-thiazolidine hydrobromide In accordance with the instructions mentioned in Example 1 (b), 4.82 g (20 mmoles) of 2-bromo-5-methoxy-1-indanone in 30 ml of acetone and 2.08 g (20 mmoles) of N,N'-dimethylthiourea in 20 ml of acetone give the crystalline end product, decomposition point 246°–248° C., which is reprecipitated from methanol/ether (decomposition point 250°–251° C.).

EXAMPLE 18

5a-Hydroxy-8-methoxy-3,4-dihydro-indano-[2,1-b]-imidazo-[1,2-d]-thiazolidine hydrobromide Analogously to Example 9, 4.82 g (20 mmoles) of 2-bromo-5-methoxy-1-indanone in 30 ml of acetone and 2.04 g (20 mmoles) of 2-imidazolidine-thione in 20 ml of acetone give the crystalline end compound which, after reprecipitation from methanol/ether, has a decomposition point of 262° C.

EXAMPLE 19

2-Benzylimino-6-chloro-3a-hydroxy-3-methyl-indano-[2,1-b]-thiazolidine hydrobromide Analogously to Example 1 (b), 2.47 g (10 mmoles) of 2-bromo-5-chloro-1-indanone (Example 1 (a)) in 30 ml of acetone and 1.80 g (10 mmoles) of N-methyl-N'-benzyl-thiourea in 20 ml of acetone give the crystalline end compound with a decomposition point of 165°–166° C.

EXAMPLE 20

8-Chloro-5a-hydroxy-3,4-dihydro-indano-[2,1-b]-imidazo-[1,2-d]-thiazolidine hydrobromide 1.98 g (10 mmoles) of 5-chloro-2-mercapto-1-indanone (Example 12 (a)) are added in portions to 1.49 g (10 mmoles) of 2-bromo-1-imidazoline in 100 ml of isopropanol and the mixture is stirred for 24 hours at room temperature. The precipitate is filtered off and reprecipitated from methanol/ether, after which the crystalline end product of decomposition point 275°–278° C. is obtained.

EXAMPLE 21

6-Chloro-3a-hydroxy-3-methyl-2-methylimino-indano-[2,1-b]-thiazolidine hydrobromide Analogously to Example 12 (b), 1.98 g (10 mmoles) of 5-chloro-2-mercapto-1-indanone (Example 12 (a)) in 30 ml of absolute tetrahydrofuran and 0.70 g (10 mmoles) of dimethylcarbodiimide give the end product which, after recrystallization from methanol/ether, decomposes at 180°–182° C.

EXAMPLE 22

7-Chloro-5a-hydroxy-3,4-dihydro-indano-[2,1-b]-imidazo-[1,2-d]-thiazolidine hydrobromide Analogously to Example 9, reaction of 4.92 g (20 mmoles) of 2-bromo-6-chloro-1-indanone (Example 7 (a)), in 50 ml of acetone with 2.04 g (20 mmoles) of 2-imidazolidine-thione in 30 ml of acetone gives the desired product (decomposition point 313°–315° C.) which, after reprecipitation from methanol/ether, decomposes at 327°–329° C.

EXAMPLE 23

6-Chloro-3a-hydroxy-3-methyl-2-methylimino-5-nitro-indano-[2,1-b]-thiazolidine hydrobromide (a) 5-Chloro-6-nitro-1-indanone 86.0 g (0.51 mole) of 5-chloro-1-indanone are introduced in portions into 540 ml of fuming nitric acid (d=1.54), cooled to −20° C., so that the temperature of the reaction mixture remains between −10° and −15° C. After the addition has ended, the mixture is subsequently stirred for 45 minutes at −15° to −20° C., the reaction solution is poured onto ice and the precipitate which has separated out is filtered off and washed with water. The crude product of melting point 110°–113° is recrystallized from ethanol, whereby the melting point of the pure 5-chloro-6-nitro-1-indanone rises to 126°–128° C.

(b) 2-Bromo-5-chloro-6-nitro-1-indanone

After adding 0.5 ml of 48% strength aqueous hydrobromic acid to a suspension of 10.70 g (50 mmoles) of 5-chloro-6-nitro-1-indanone in 60 ml of glacial acetic acid, a solution of 7.99 g (50 mmoles) of bromine in 50 ml of glacial acetic acid is added dropwise, whereupon a clear solution forms, from which a precipitate separates out after some time.

After the dropwise addition has ended, the mixture is subsequently stirred for one hour and the reaction mixture is poured onto ice, to which 0.5 g of NaHSO₃ has been added. The substance, which has precipitated in the crystalline form, is filtered off and washed with water and the crude product (melting point 125°–126° C.) is recrystallized from ethanol. The pure 2-bromo-5-chloro-6-nitro-1-indanone melts at 155°–157° C.

(c) 6-Chloro-3a-hydroxy-3-methyl-2-methylimino-5-nitro-indano-[2,1-b]-thiazolidine hydrobromide Analogously to Example 1 (b), 5.80 g (20 mmoles) of 2-bromo-5-chloro-6-nitro-1-indanone in 40 ml of acetone and 2.08 g (20 mmoles) of N,N'-dimethylthiourea in 30 ml of acetone give the crystalline end compound with a decomposition point of 197°–198° C.

EXAMPLE 24

8-Chloro-5a-hydroxy-7-nitro-3,4-dihydro-indano-[2,1-b]-imidazo-[1,2-b]-thiazolidine hydrobromide Analogously to Example 9, after reacting 4.34 g (15 mmoles) of 2-bromo-5-chloro-6-nitro-1-indanone (Example 23 (b) in 50 ml of acetone with 1.53 g (15 mmoles) of 2-imidazolidine-thione, suspended in 30 ml of acetone, the crystalline end product with a decomposition point of 200° C. is isolated.

EXAMPLE 25

6-Chloro-3-cyclopropyl-2-cyclopropylimino-3a-hydroxy-indano-[2,1-b]-thiazolidine hydrobromide In accordance with the procedure described in Example 1 (b), 2.47 g (10 mmoles) of 2-bromo-5-chloro-1-indanone (Example 1 (a)) in 30 ml of acetone and 1.56 g (10 mmoles) of N,N'-dicyclopropyl-thiourea in 20 ml of acetone give the colorless crystalline end product of decomposition point 177°–178° C.

EXAMPLE 26

5a-Hydroxy-3,4-dihydro-indano-[2,1-b]-imidazo-[1,2-d]-thiazolidine hydrobromide

A mixture of 2.13 g (10 mmoles) of 2-bromo-1-indanol and 1.02 g (10 mmoles) of 2-imidazolidine-thione in 100 ml of isopropanol is stirred for 24 hours at room temperature. The precipitate is filtered off and dissolved in 200 ml of methylene chloride and, after adding 30 g of active manganese dioxide, the reaction mixture is stirred for 48 hours at room temperature. The precipitate is filtered off and the filtrate is concentrated in vacuo. The amorphous residue is reprecipitated from methanol/ether and gives the end product of decomposition point 262°–264° C.

EXAMPLE 27

8-Chloro-5a-hydroxy-3,4-dihydro-indano-[2,1-b]-imidazo-[1,2-d]-thiazolidine hydrobromide A solution of 0.6 g of sodium borohydride in 5 ml of methanol is added dropwise to a solution of 2.45 g (10 mmoles) of 2-bromo-5-chloro-1-indanone (Example 1 (a)) in 20 ml of methanol at +5° C. and the mixture is then stirred for 1 hour at room temperature. The reaction mixture is acidified with 2 N hydrochloric acid, whilst cooling, and the solvent is distilled off under reduced pressure. After adding 100 ml of water, the mixture is extracted with 200 ml of chloroform, the organic phase is dried over Na₂SO₄ and the solvent is evaporated off in a rotary evaporator. The solid 2-bromo-5-chloro-1-indanol which remains is taken up in 100 ml of isopropanol and 1.02 g (10 mmoles) of 2-imidazolidine-thione are added to the reaction mixture. After stirring for 24 hours, the precipitate is filtered off and reacted with 30 g of active manganese dioxide in accordance with the procedure indicated in Example 26. The crude product is reprecipitated from methanol/ether, after which the end product of decomposition point 276°–278° C. is obtained.

EXAMPLE 28

8-Chloro-5a-hydroxy-3,4-dihydro-indano-[2,1-b]-imidazo-[1,2-d]-thiazolidine hydrochloride A suspension of 0.5 g (1.43 mmoles) of 8-chloro-5a-hydroxy-3,4-dihydro-indano-[2,1-b]-imidazo-[1,2-d]-thiazolidine hydrobromide (Example 10) in 20 ml of water is adjusted to a pH value of 9.5 by adding 2 N NaOH dropwise. After stirring for 15 minutes, the precipitate is filtered off and suspended in 10 ml of acetic acid ethyl ester. Ethereal hydrochloric acid is added to the suspension, the mixture is stirred for 30 minutes and the precipitate is filtered off. This gives the end product of decomposition point 248°–250° C.

EXAMPLE 29

3a-Hydroxy-3-methyl-2-methylimino-3a,8,9,9a-tetrahydro-naphtho-[2,1-b]-thiazolidine hydrobromide (a) 3–5 ml of a solution of 4.8 g of bromine (0.03 mole) in 15 ml of ethyl acetate are rapidly added dropwise at room temperature to a stirred solution of 4.38 g of 1-tetralone (0.03 mole) in 45 ml of ethyl acetate. If the bromine is not immediately decolorized, hydrogen bromide gas is passed into the reaction mixture for a few seconds.

After adding the rest of the bromine solution dropwise at 15°–20° C., the mixture is stirred for a further 5 minutes, the solvent is distilled off under reduced pressure and the 2-bromo-1-tetralone, obtained as an oil, is reacted immediately and without further purification.

(b) 0.03 mole of 2-bromo-1-tetralone is dissolved in 20 ml of ethyl acetate and a solution of 3.12 g (0.03 mole) of N,N'-dimethyl-thiourea in 10 ml of ethyl acetate is added at room temperature, whilst stirring. After about 30 minutes, the thiazolidine begins to precipitate. The mixture is stirred for a further 4 hours and the crystals are filtered off and washed with ethyl acetate. This gives colorless crystals of melting point 139°–140° C. (decomposition).

EXAMPLE 30

5a-Hydroxy-3,4,5,5a,10,11-hexahydro-11aH-naphtho-[2,1b]-imidazo[1,2-d]-thiazolidine hydrobromide obtained by reacting 0.03 mole of 2-bromo-1-tetralone (Example 29 (a)) with 3.06 g (0.03 mole) of pulverulent 2-imidazolidine-thione in 40 ml of methanol.

After stirring for 40 hours at room temperature, 80 ml of ether are added and the amorphous precipitate is made to crystallize, using 50 ml of acetone.

Colorless crystals. Melting point 250°–255° C. (decomposition).

EXAMPLE 31

6a-Hydroxy-3,4,5,6,6a,11,12,12a-octahydronaphtho-[2,1-b]-pyrimido[1,2-d]-thiazolidine hydrobromide is obtained by reacting 0.03 mole of 2-bromo-1-tetralone (Example 29 (a)) with 3.48 g (0.03 mole) of 3,4,5,6-tetrahydro-2-pyrimidine-thiol in 50 ml of acetone. After warming briefly to 40° C. and subsequently stirring at room temperature overnight, the precipitate is filtered off and rinsed with acetone. Colorless crystals. Melting point 246° C. (decomposition).

EXAMPLE 32

2-Benzylimino-3a-hydroxy-3-methyl-3a,8,9,9a-tetrahydronaphtho-[2,1-b]-thiazolidine hydrobromide is obtained, in accordance with the instructions indicated in Example 31, by reacting 2-bromo-1-tetralone with N-benzyl-N'-methylthiourea. After leaving the reaction mixture to stand overnight at room temperature, the solvent is driven off under reduced pressure and the residue is allowed to crystallize, using ethyl acetate.

Colorless crystals. Melting point 203° C. (decomposition).

EXAMPLE 33

3a-Hydroxy-3,8-dimethyl-2-methylimino-3a,8,9,9a-tetrahydronaphtho-[2,1-b]-thiazolidine hydrobromide (a) 4.8 g (0.03 mole) of 4-methyl-1-tetralone are reacted with 4.8 g (0.03 mole) of bromine in ethyl acetate, analogously to the instructions indicated in Example 29 (a), to give 2-bromo-4-methyl-1-tetralone. The oily product is further processed immediately without further purification.

(b) The amorphous 2-bromo-4-methyl-1-tetralone (0.03 mole) is reacted, in 40 ml of ethyl acetate, with 3.12 g (0.03 mole) of N,N'-dimethylthiourea for 12 hours at room temperature and the amorphous precipitate is made to crystallize, using acetone. Melting point 231° C. (decomposition).

EXAMPLE 34

6a-Hydroxy-10-methyl-3,4,5,5a,10,11-hexahydro-11aH-naphtho-[2,1-b]-imidazo-[1,2-d]-thiazole hydrobromide is obtained analogously to the instructions indicated in Example 30 from 2-imidazolidine-thione and 2-bromo-4-methyl-1-tetralone. Colorless crystals. Melting point 218°–221° C. (decomposition).

EXAMPLE 35

6-Chloro-3a-hydroxy-3-methyl-2-methylimino-3a,8,9,9a-tetrahydronaphtho-[2,1-b]-thiazolidine hydrobromide (a) 5 g of 6-chloro-1-tetralone are reacted with 4.4 g of bromine in ethyl acetate analogously to the instructions indicated in Example 29 (a). After distilling off the solvent under reduced pressure, 2-bromo-6-chloro-1-tetralone is obtained as an amorphous residue, which is used without further purification.

(b) The amorphous 2-bromo-6-chloro-1-tetralone is reacted with 2.9 g of N,N'-dimethylthiourea, analogously to the instructions indicated in Example 29 (b), and the amorphous precipitate is made to crystallize, using a little acetone. Colorless crystals. Melting point 249° C. (decomposition).

EXAMPLE 36

5-Chloro-3a-hydroxy-3-methyl-2-methylimino-3a,8,9,9a-tetrahydronaphtho-[2,1-b]-thiazolidine hydrobromide (a) In accordance with the instructions indicated in Example 29 (a), 4 g (0.022 mole) of 7-chloro-1-tetralone are reacted with 3.53 g (0.022 mole) of bromine in ethyl acetate, the mixture is worked up and the amorphous 2-bromo-7-chloro-1-tetralone is further used without purification.

(b) Analogously to the instructions indicated in Example 29 (b), 0.022 mole of 2-bromo-7-chloro-1-tetralone is reacted with 2.29 g (0.022 mole) of N,N'-dimethylthiourea and the mixture is worked up. Colorless crystals. Melting point 263° C. (decomposition).

EXAMPLE 37

7-Chloro-5a-hydroxy-3,4,5,5a,10,11-hexahydro-11aH-naphtho-[2,1-b]-imidazo-[1,2-d]-thiazole hydrobromide Analogously to the instructions indicated in Example 31, 0.022 mole of 2-bromo-7-chloro-1-tetralone is reacted with 2.24 g (0.022 mole) of 2-imidazolidine-thione and the mixture is worked up. Colorless crystals. Melting point 250°–255° (decomposition).

EXAMPLE 38

3a-Hydroxy-3-methyl-2-methylimino-5-nitro-3a,8,9,9a-tetrahydronaphtho-[2,1-b]-thiazolidine hydrobromide (a) In accordance with the instructions indicated in Example 29 (a), 5 g (0.03 mole) of 7-nitro-1-tetralone are reacted with 4.8 g (0.03 mole) of bromine, the mixture is worked up and the amorphous 2-bromo-7-nitro-1-tetralone is further used without purification.

(b) In accordance with the instructions indicated in Example 29 (b), 0.03 mole of 2-bromo-7-nitro-1-tetralone is reacted with 3.12 g (0.03 mole) of N,N'-dimethylthiourea and the mixture is worked up. Colorless crystals. Melting point 240° C. (decomposition).

EXAMPLE 39

5a-Hydroxy-7-nitro-3,4,5,5a,10,11-hexahydro-11aH-naphtho-[2,1-b]-imidazo-[1,2-d]-thiazole hydrobromide is obtained, analogously to the instructions indicated in Example 31, by reacting 0.03 mole of 2-bromo-7-nitro-1-tetralone with 3.06 g (0.03 mole) of powdered 2-imidazolidine-thione. Colorless crystals. Melting point 279°–282° C. (decomposition).

EXAMPLE 40

5a-Hydroxy-3,3-dimethyl-3,4,5,5a,10,11-hexahydro-11aH-naphtho-[2,1-b]-imidazo-[1,2-d]-thiazole hydrobromide is obtained from 2-bromo-1-tetralone and 4,4-dimethyl-2-imidazolidine-thione, in accordance with the instructions indicated in Example 29 (b). Colorless crystals. Melting point 258° C. (decomposition).

EXAMPLE 41

6-Chloro-3a-hydroxy-3-methyl-2-methylimino-indano-[2,1-b]-thiazolidine hydrochloride

(a) 2,5-Dichloro-1-indanone

Hydrogen chloride gas is passed into a solution of 10.11 g (60 mmoles) of 5-chloro-1-indanone in 50 ml of glacial acetic acid at 10°-15° C. for 30 minutes. 4.25 g (60 mmoles) of condensed chlorine are then allowed to flow slowly into the solution at 10° C. and the mixture is allowed to come gradually to room temperature and is subsequently stirred for 3 hours. After standing overnight, the solution is poured onto ice, the oil which separates out is extracted with acetic acid ethyl ester and the solvent is distilled off under reduced pressure. The oil which remains crystallizes on standing. The product can be recrystallized from petroleum ether and then melts at 63°-66° C.

(b) 6-Chloro-3a-hydroxy-3-methyl-2-methylimino-indano-[2,1-b]-thiazolidine hydrochloride A solution of 1.05 g (10 mmoles) of N,N'-dimethylthiourea in 30 ml of acetone is added to a solution of 2.01 g (10 mmoles) of 2,5-dichloro-1-indanone in 50 ml of acetone and the mixture is stirred for 5 hours at room temperature. The reaction solution is concentrated, the viscous residue is dissolved in a little methanol and the end product is precipitated by slowly adding diethyl ether. The oil which initially separates out crystallizes on triturating and gives the crystalline end compound of decomposition point 265°-267° C.

EXAMPLE 42

8-Chloro-5a-hydroxy-3,4-dihydro-indano-[2,1-b]-imidazo-[1,2-d]-thiazolidine hydrochloride A solution of 1.02 g (10 mmoles) of 2-imidazolidinethione in 30 ml of acetone is added to a solution of 2.01 g (10 mmoles) of 2,5-dichloro-1-indanone (Example 41 (a)) in 50 ml of acetone and the mixture is then stirred for 5 hours at room temperature. The end product which has precipitated is filtered off, and this product decomposes at 248°-250° C.

What is claimed is:
1. Thiazolidine derivatives of the general formula I

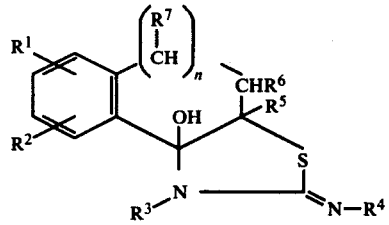

in which $R^1$ denotes hydrogen, a methyl group, halogen, trifluoromethyl or an alkoxy group with 1-3 C atoms, $R^2$ denotes hydrogen, a methyl group, halogen or a nitro group, $R^3$ and $R^4$ are the same or different and denote alkyl or alkenyl with 1-4 C atoms, phenylalkyl with 1-2 C atoms in the alkyl part or cycloalkyl with 3-6 C atoms, $R^5$, $R^6$ and $R^7$ denote hydrogen or an alkyl radical with 1-3 C atoms and n is 0-2, or acid addition salts thereof with pharmaceutically acceptable acids.

2. 6-Chloro-3a-hydroxy-3-methyl-2-methylimino-indano-[2,1-b]-thiazolidine hydrochloride or hydrobromide.

3. 3-Allyl-2-allylimino-6-chloro-3a-hydroxy-indano-[2,1-b]-thiazolidine hydrobromide.

4. 3a-Hydroxy-3-methyl-2-methylimino-indano-[2,1-b]-thiazolidine hydrobromide.

5. The compounds as defined in claim 1 wherein n is 1 or 2.

6. The hydrochloride salt of the compound of claim 2.

7. The hydrobromide salt of the compound of claim 2.

8. A pharmaceutical preparation of a compound as defined in claim 1.

9. A pharmaceutical preparation for the treatment of obesity or a lipid metabolism disorder of a compound as defined in claim 1 in an effective unit dosage.

10. A process for the manufacture of pharmaceutical preparations for the treatment of obesity and lipid metabolism disorders of a compound as defined in claim 1, optionally with pharmaceutical excipients and/or stabilizers which comprises preparing a dosage form of said compound in an effective amount suitable for therapeutic purposes.

11. A process for the treatment of obesity and/or lipid metabolism disorders, which comprises administering an effective amount of a compound as defined in claim 1.

* * * * *